United States Patent [19]
Fowler

[11] 3,939,153
[45] Feb. 17, 1976

[54] PROCESS FOR PRODUCING CAPROLACTAM

[75] Inventor: Frank C. Fowler, Kansas City, Mo.

[73] Assignee: Hillyard Chemical Company, St. Joseph, Mo.

[22] Filed: Aug. 9, 1974

[21] Appl. No.: 496,258

[52] U.S. Cl. .......................................... 260/239.3 A
[51] Int. Cl.² .......................................... C07D 201/12
[58] Field of Search .............................. 260/239.3 A

[56] References Cited
UNITED STATES PATENTS

| | | | |
|---|---|---|---|
| 2,667,483 | 1/1954 | Zeegers | 260/239.3 A |
| 2,930,790 | 3/1960 | Weise | 260/239.3 A |
| 3,182,055 | 5/1965 | Bonfield et al. | 260/239.3 A |

FOREIGN PATENTS OR APPLICATIONS

| | | | |
|---|---|---|---|
| 44,018 | 12/1965 | Germany | 260/239.3 A |

*Primary Examiner*—Henry R. Jiles
*Assistant Examiner*—Robert T. Bond

[57] ABSTRACT

A non-catalytic method is provided for depolymerizing nylon-6 to produce e-caprolactam. The nylon, as a melt is continuously fed to a reaction zone together with superheated steam and undecomposed polymer melt is continuously withdrawn from the reaction zone together with steam and polymer decomposition products. Caprolactam is recovered from the polymer decomposition products.

8 Claims, 1 Drawing Figure

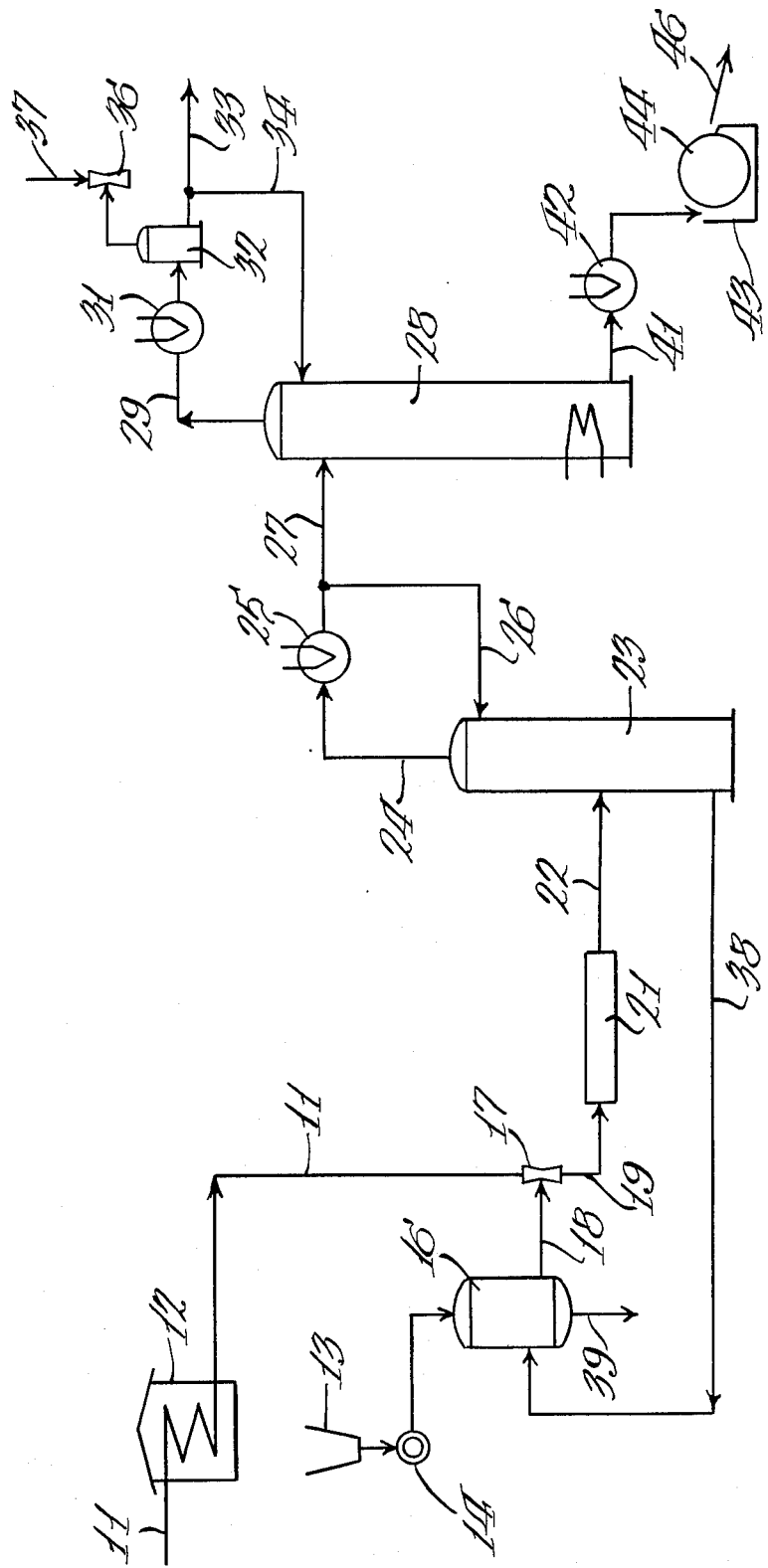

PROCESS FOR PRODUCING CAPROLACTAM

This invention relates to the production of e-caprolactam by the non-catalytic depolymerization of nylon-6.

Nylon-6, a linear polyamide made by the polymerization of e-caprolactam, is used extensively in the manufacture of molded articles, films and fibers. During the fabrication of useful products from nylon-6, waste or scrap polymer is produced as an unavoidable by-product of the manufacturing process.

To minimize the cost of waste or scrap polymer, depolymerization processes have been developed for conversion of the nylon-6 to its constituent monomer by depolymerization with steam in the presence of phosphoric acid. The phosphoric acid is generally termed a "catalyst" in the system but it is known that it is consumed during the reaction and produces phosphorus-containing by-products which must be removed before the caprolactam product is suitable for polymerization.

In addition, the presence of phosphoric acid in the system creates corrosion problems unless expensive corrosion-proof equipment is used.

Bonfield et al. U.S. Pat. No. 3,182,055, issued May 4, 1965, relates to a method of depolymerizing nylon-6 with steam in the presence of a lesser amount of phosphoric acid than the amount which had previously been used. In order to operate with less phosphoric acid than had previously been considered essential, the Bonfield et al. process utilizes a preformed pool of polymer melt which is maintained in the reactor while polymer melt and steam are continuously supplied and steam and e-caprolactam are continuously withdrawn.

Reduction of the amount of phosphoric acid, in the Bonfield et al. process, reduces but does not eliminate the adverse effects of phosphoric acid on the products of the process. In addition, the process is continuous only for a limited period and must be discontinued as unreactable residual products accumulate in the pool of polymer melt and fill the vessel.

In accordance with the present invention there is provided a process for producing e-caprolactam from a polymer thereof which comprises continuously introducing into a reaction zone a melt of said polymer, continuously introducing high temperature steam into said reaction zone as the sole deploymerizing agent therein, continuously withdrawing from said reaction zone, steam, polymer degradation products and undecomposed polymer melt, maintaining said reaction zone at a temperature of at least about 600°F. and recovering e-caprolactam from said polymer degradation products as a product of said process.

Preferably, the temperature of the polymer melt introduced into the reaction zone is in the range from about 450° to about 600°F.; and the steam is introduced at a temperature in the range from about 750° to about 1350°F. The steam is preferably introduced into the reaction in amounts from about 2 to 10 times the weight of the polymer melt introduced.

In the preferred system the polymer melt is injected into a stream of superheated steam and a combined stream of polymer melt and steam is introduced into one end of an elongated reaction zone while a combined stream of undecomposed polymer melt, steam, and polymer degradation products is withdrawn at the opposite end of the zone. The depolymerization reaction is endothermic and the entrance end of the reaction is generally at a higher temperature than the exit end unless heat is added to the reaction zone from an external source. The average temperature in the reaction zone is generally in the range from about 650° to about 1250°F.

The elongated reaction zone is generally tubular and the combined stream of polymer melt and steam generally passes through the reaction zone with the melt flowing as a film along the inner tubular walls. The average residence time for the polymer melt in the reaction zone is from about ½ minute to about 10 minutes.

From the reaction zone the products, including undecomposed polymer melt, polymer degradation products and steam, are passed into a first fractionation column in which a bottoms fraction comprising undecomposed polymer melt and high boiling decomposition products is withdrawn for recycling to the reacton zone; and an overhead fraction comprising e-caprolactam and steam is withdrawn for the recovery of e-caprolactam therefrom.

The invention may be more readily understood from the drawing which is a semi-schematic flow diagram of the process of the invention.

As shown in the drawing, steam from an external source is passed through line 11 into and through superheater which raises its temperature to about 776°F. at a pressure of about 115 psia. Scrap nylon 6 in hopper 13 is passed through comminutor 14 which breaks or cuts the scrap polymer into pieces small enough to be melted easily. The comminuted scrap is then passed into melt tank 16 in which the scrap is melted and heated to a temperature of about 600°F. at which temperature it is sufficiently fluent to flow without difficulty.

The superheated steam in line 11 is passed through ejector 17 as a high velocity stream and melted nylon is drawn into the ejector through line 18, the steam and nylon melt leaving the ejector as a combined stream in line 19 at a temperature of about 700°F. and passing into one end of tubular, elongated reactor 21.

In the reactor, the nylon-6 is partially decomposed and the endothermic decomposition reaction reduces the temperature of the material therein to about 650°F. at the point of emergence from the reactor. Typically, the average residence time for the nylon melt in the reactor is from about one to about 40 minutes and the average residence time for steam in the reactor is from about 0.01 to about ten seconds.

Steam and a nylon melt decomposition product pass out of reactor 21 as a combined stream in line 22; and the stream is introduced into nylon column 23 at a midpoint thereof for distillation therein. In the nylon column, low boiling constituents, including steam and nylon decomposition products, pass overhead in vapor phase through line 24 and condenser 25, with a portion of the decomposition products being reliquefied in the latter and recycled to the nylon column through line 26. The remainder of the vaporized product is passed through line 27 into monomer column 28 at an upper portion thereof for distillation therein.

In the monomer column distillation is carried out at subatmospheric pressure with steam passing overhead through line 29 to condenser 31 in which it is condensed. The condensate is passed to collection vessel 32 from which water is withdrawn from the system through line 33. A portion of the condensed water is recycled to the monomer column through line 34 for refluxing. Ejector 36, into which steam is introduced through line 37 serves as a means for maintaining a subatmospheric pressure in the monomer column.

Higher boiling materials, consisting primarily of unconverted polymer and byproduct oligomers, are withdrawn from the nylon column through line 38 at a temperature of about 600°F. and introduced into melt tank 16 to be blended therein with fresh polymer and then fed back into the system through line 18, as discused above. A small amount of melt from tank 16 is withdrawn, continuously or periodically, through line 39 to prevent excessive buildup of intractable materials.

The higher builing material in the monomer column, consisting substantially entirely of e-caprolactam in liquid phase is withdrawn through line 41, partially cooled in heat exchanger 42 and passed to flaker 43 in which the monomer is solidified on the surface of cooled, rotating, horizontally disposed cylinder 44 and is scraped off in flake form by doctor blade 46 for removal from the system as the product thereof.

In a typical system having a capacity of about one million pounds per year based on operations 250 days per year and seven hours per day, steam is fed to the superheater at 2884 pounds per hour and fresh nylon-6 polymer at 600 pounds per hour. In this typical system about 20% of the nylon-6 passing through the reactor is depolymerized to e-caprolactam and the remainder, about 2284 pounds per hour is recycled to the melt tank from the bottom of the nylon column, as described above, About 200 pounds per day of material is discharged from the melt tank to prevent buildup of intractably byproducts.

In the typical system described, the monomer column is operated at an absolute pressure of about 50 millimeters of mercury and at an average temperature of about 320°F. The water discharged from the collection vessel is about 2884 pounds per hour; and the caprolactam recovered as the product of the process is about 571 pounds per hour.

The process described above provides the production of e-caprolactam from nylon-6 without the use of phosphoric acid or other catalysts. As a result, corrosion problems in the reactor and accessory equipment are substantially eliminated and the necessity for purifying the monomer product of phosphorus-containing byproducts is completely eliminated. The monomer recovered from the process is equivalent in quality to virgin e-caprolactam.

The invention has been described with respect to a specific embodiment but it will be understood by those skilled in the art that modifications may be without departing from the essence of this invention.

What is claimed is:

1. A process for producing e-caprolactam from a polymer thereof which comprises continuously introducing into a reaction zone a melt of said polymer, continuously introducing high temperature steam into said reaction zone as the sole depolymerizing agent therein, continuously withdrawing from said reaction zone, steam, polymer degradation products and undecomposed polymer melt, maintaining said reaction zone at a temperature of at least about 600°F. and recovering e-caprolactam from said polymer degradation products as a product of said process.

2. The process of claim 1 wherein said polymer melt is introduced into said reaction zone at a temperature between about 450° and about 600°F. and steam is introduced into said reaction zone at a temperature between about 750° and about 1300°F. and said reaction zone is at an average temperature between about 650° and about 1250°F.

3. The process of claim 1 wherein said steam is supplied to said reaction zone in an amount between about 2 and about 10 times the weight of the polymer melt supplied thereto.

4. The process of claim 3 wherein said polymer melt is injected into a stream of said steam and wherein said steam and polymer melt are introduced into said reaction zone as a combined stream.

5. The process of claim 1 wherein the average residence time of said polymer melt in said reaction zone is from about ½ minute to about 10 minutes.

6. The process of claim 1 wherein at least a portion of said undecomposed polymer melt is recycled to said reaction zone.

7. The process of claim 6 wherein at least a portion of said polymer degradation products is recycled to said reaction zone after removal of at least a portion of the 3-caprolactam therein.

8. A process for producing e-caprolactam from a polymer thereof which comprises maintaining a melt of said polymer at a temperature between about 400° and about 600°F., continuously injecting a portion of said melt into a stream of steam heated to between about 750° and about 1000°F. in a weight ratio between about 1/10 to about ½ pounds of melt to one pound of steam to produce a combined stream of polymer melt and steam, continuously introducing said combined stream into an elongated reaction zone, said steam being the sole depolymerizing agent in said zone, maintaining said reaction zone at an average temperature between about 650° and about 1250°F., maintaining said polymer melt in said reaction zone for an average residence time between about ½ minute and about 10 minutes, continuously withdrawing from said reaction zone, steam, polymer degradation products and undecomposed polymer melt, recovering e-caprolactam from said polymer degradation products and recycling to said reaction zone at least a portion of said undecomposed polymer melt and at least a portion of said polymer degradation products from which said e-caprolactam has been removed.

* * * * *